(12) United States Patent
Tateshita et al.

(10) Patent No.: US 11,389,048 B2
(45) Date of Patent: Jul. 19, 2022

(54) ENDOSCOPIC IMAGE OBSERVATION SUPPORT SYSTEM

(71) Applicant: OLYMPUS CORPORATION, Tokyo (JP)

(72) Inventors: Isao Tateshita, Tokyo (JP); Kei Kikuchi, Tokyo (JP); Hirokazu Nishimura, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 556 days.

(21) Appl. No.: 16/034,415

(22) Filed: Jul. 13, 2018

(65) Prior Publication Data

US 2018/0325356 A1    Nov. 15, 2018

Related U.S. Application Data

(63) Continuation of application No. PCT/JP2016/080326, filed on Oct. 13, 2016.

(30) Foreign Application Priority Data

Jan. 15, 2016  (JP) .............................. JP2016-006616

(51) Int. Cl.
  *A61B 1/00*     (2006.01)
  *A61B 1/04*     (2006.01)

(52) U.S. Cl.
  CPC ........ *A61B 1/00055* (2013.01); *A61B 1/0002* (2013.01); *A61B 1/00006* (2013.01);
  (Continued)

(58) Field of Classification Search
  CPC .............. A61B 1/00006; A61B 1/0002; A61B 1/00055; A61B 1/041
  See application file for complete search history.

(56) References Cited

U.S. PATENT DOCUMENTS

2011/0249952 A1* 10/2011 Taniguchi .......... A61B 1/00009
                                                    386/230
2013/0229503 A1*  9/2013 Taniguchi .............. G16H 30/20
                                                     348/65

FOREIGN PATENT DOCUMENTS

JP        2007-260064 A     10/2007
JP        2007260064      * 10/2007  ............... A61B 6/00
                    (Continued)

OTHER PUBLICATIONS

International Search Report dated Dec. 27, 2016 issued in International Application No. PCT/JP2016/080326.
(Continued)

*Primary Examiner* — Aaron B Fairchild
(74) *Attorney, Agent, or Firm* — Scully, Scott, Murphy & Presser, P.C.

(57) ABSTRACT

A playback processing unit causes a display device to display an endoscopic image recorded in an endoscopic image recording unit. A display time setting unit sets a display time of endoscopic images displayed by the playback processing unit on the display device in the order of imaging. A display time measurement unit measures the display time of each endoscopic image. A time information storage unit stores information related to the display time measured by the display time measurement unit. An acknowledgment unit acknowledges a user operation input. The playback processing unit causes the display device to display the endoscopic image in accordance with the user operation input acknowledged by the acknowledgment unit. The time information storage unit stores information related to a cumulative display time of each endoscopic image.

10 Claims, 7 Drawing Sheets

(52) U.S. Cl.
CPC ............ *A61B 1/00045* (2013.01); *A61B 1/04* (2013.01); *A61B 1/041* (2013.01)

(56) References Cited

FOREIGN PATENT DOCUMENTS

| | | |
|---|---|---|
| JP | 2009-039449 A | 2/2009 |
| JP | 2009-082182 A1 | 4/2009 |
| JP | 2015-077234 A | 4/2015 |
| WO | 2011/013475 A1 | 2/2011 |
| WO | 2013/024687 A1 | 2/2013 |

OTHER PUBLICATIONS

Japanese Office Action dated Nov. 7, 2017 in Japanese Patent Application No. 2017-549101.
International Preliminary Report on Patentability dated Jul. 17, 2018 together with the Written Opinion received in related International Application No. PCT/JP2016/080326.

* cited by examiner

FIG.5A

| OBSERVED IMAGE | REFERENCE OBSERVATION TIME |
|---|---|
| IMAGE CAPTURED AT HIGH SPEED | 3 SECONDS |
| IMAGE CAPTURED AT NORMAL SPEED | 0.5 SECONDS |
| IMAGE CAPTURED AT LOW SPEED | 0.1 SECONDS |

| OBSERVED IMAGE | REFERENCE OBSERVATION TIME |
|---|---|
| IMAGE OF INTEREST | 7 SECONDS |
| IMAGE CAPTURED AT DISTANCE OF 3 CM OR LESS FROM IMAGE OF INTEREST | 5 SECONDS |
| IMAGE CAPTURED AT DISTANCE OF MORE THAN 3 CM AND EQUAL TO OR LESS THAN 7 CM | 2 SECONDS |

| OBSERVED IMAGE | REFERENCE OBSERVATION TIME |
|---|---|
| IMAGE OF INTEREST | 7 SECONDS |
| IMAGE CAPTURED AT AN INTERVAL OF 5 SECONDS OR LESS | 5 SECONDS |
| IMAGE CAPTURED AT AN INTERVAL LONGER THAN 5 SECONDS AND EQUAL TO OR LESS THAN 10 SECONDS | 2 SECONDS |

54

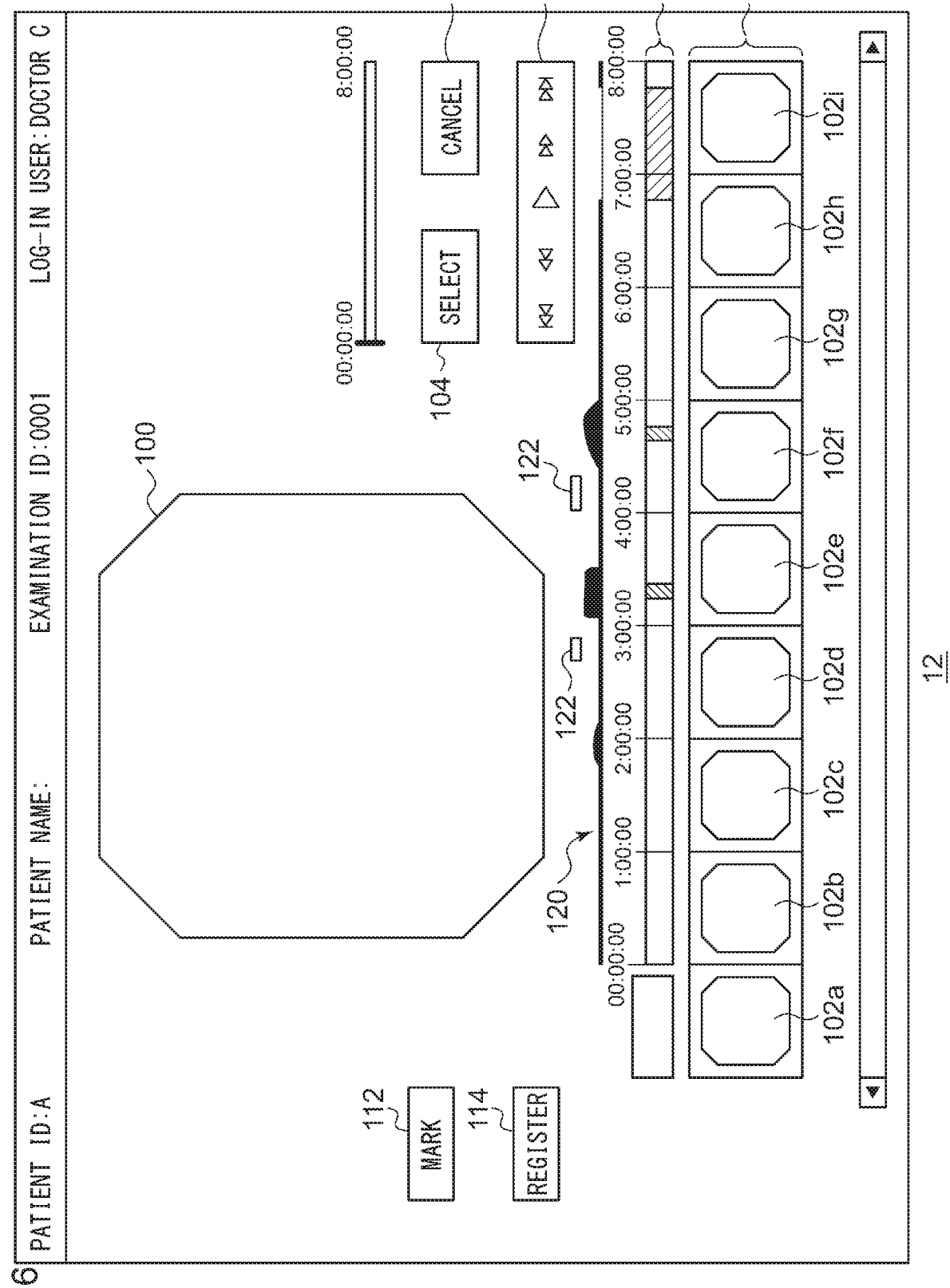

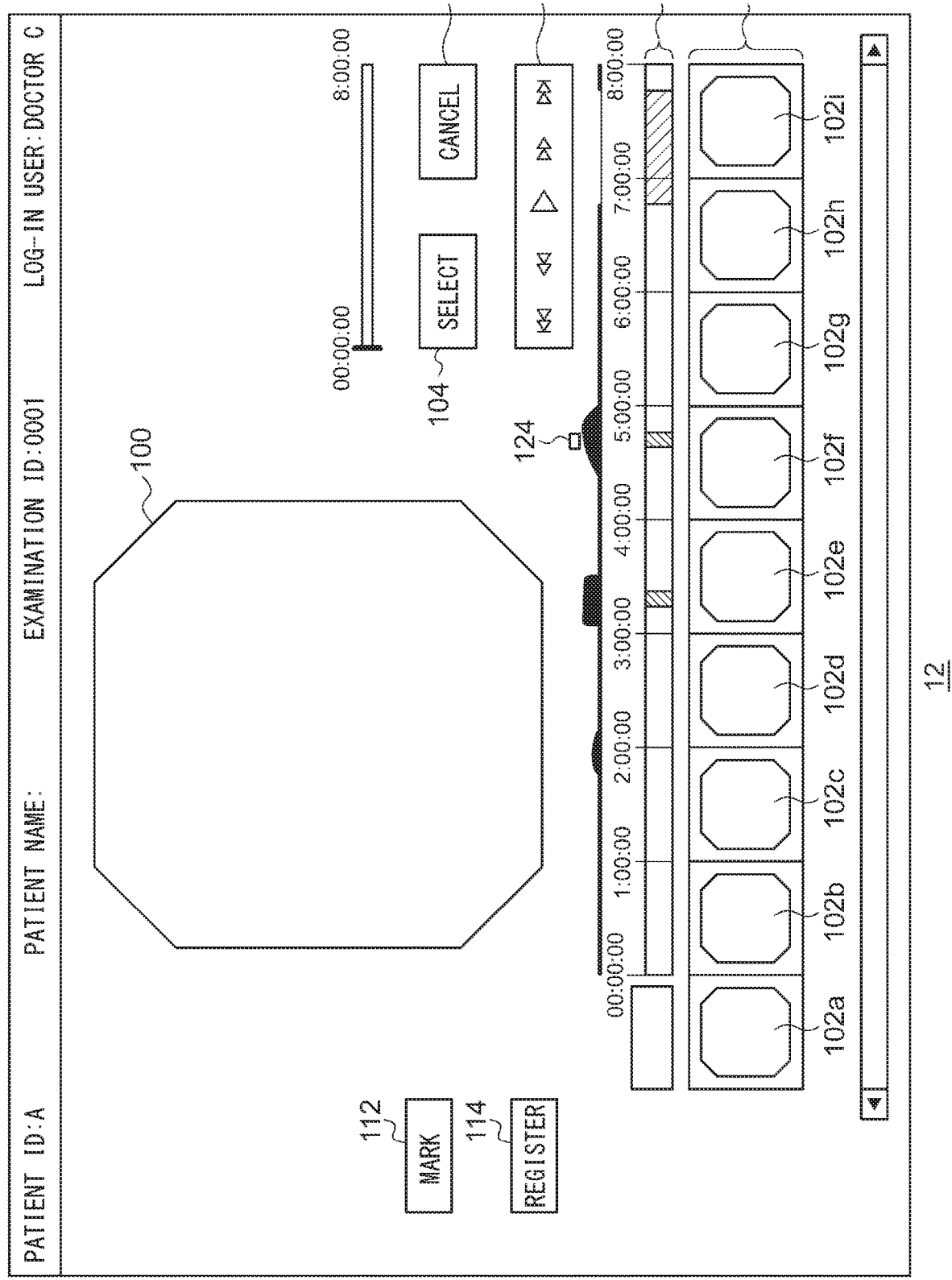

ENDOSCOPIC IMAGE OBSERVATION SUPPORT SYSTEM

CROSS-REFERENCE TO RELATED APPLICATIONS

This application is based upon and claims the benefit of priority from the prior Japanese Patent Applications No. 2016-006616, filed on Jan. 15, 2016, and International Application No. PCT/JP2016/080326, filed on Oct. 13, 2016, the entire contents of which are incorporated herein by reference.

BACKGROUND OF THE INVENTION

1. Field of the Invention

The present invention relates to a system for supporting observation of images captured by a capsule endoscope.

2. Description of the Related Art

JP2009-82182 discloses an examination support apparatus that measures a time taken for interpreting a medical image and compares the measured time with the standard interpretation time. If the interpretation time is too short, the apparatus displays a message that warns the possibility of an operational error. Meanwhile, if the interpretation time is too long, it is judged that reinterpretation is necessary and the judgment is recorded in the report database along with the result of interpretation. JP2015-77234 discloses a technology of estimating a position of the capsule endoscope using a signal level (a received signal intensity) of the signal received by a plurality of antenna elements and calculating a moving speed of the capsule endoscope based on a distance between two locations of the capsule endoscope estimated and a time of movement between the two locations.

In a capsule endoscopic examination, the patient swallows a capsule having a built-in ultracompact camera from the mouth, with a plurality of antennas being fixed to the abdomen and a recorder being attached to the waist by a belt. The capsule captures still images periodically as it moves through the digestive tract and transfers captured images to the recorder from the antennas. After about 8 hours, the antennas and the recorder are collected, and the images recorded in the recorder are recorded in a database in medical facilities.

The image interpreter then observes images played back and displayed in the order of imaging and identifies an image found to include an abnormality. Since a total of 10000~200000 images are captured by the capsule endoscope, the load imposed on the image interpreter is quite heavier than the load imposed in other types of image interpretation. It is therefore preferable to record, for each act of image observation, information that serves as an indicator that can be referred to to later check whether image observation has been properly performed.

Double image interpretation by two image interpreting doctors is sometimes practiced to reduce the likelihood of overlooking. Recently, double image interpretation in which a technician assist in diagnostic imaging and a doctor completes an image interpretation report is proposed. In double image interpretation, the two image interpreters independently observe endoscopic images and create an image interpretation report. It is expected that the image interpreter observing images later can perform efficient image observation by knowing a situation of observation by the image interpreter who observed the images earlier. In this regard, building of a system for generating an indicator indicating a situation of observation by an earlier image interpreter and letting the later image interpreter know the situation of observation by the earlier image interpreter is called for.

SUMMARY OF THE INVENTION

In this background, a purpose of the present invention is to provide a technology of supporting observation of capsule endoscopic images.

An endoscopic image observation support system according to one embodiment of the present invention supports observation of endoscopic images captured by a capsule endoscope and comprises: an endoscopic image recording unit that records a plurality of endoscopic images captured by a capsule endoscope; a playback processing unit that causes a display device to display an endoscopic image recorded in the endoscopic image recording unit; a display time setting unit sets a display time of endoscopic images displayed by the playback processing unit on the display device in the order of imaging; a display time measurement unit measures the display time of each endoscopic image; a time information storage unit stores information related to the display time measured by the display time measurement unit; and an acknowledgment unit acknowledges a user operation input. The playback processing unit causes the display device to display the endoscopic image in accordance with the user operation input acknowledged by the acknowledgment unit, and the time information storage unit stores information related to a cumulative display time of each endoscopic image.

Optional combinations of the aforementioned constituting elements, and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 5A-5C show examples of reference observation time retained in the reference time retaining unit;

FIG. 6 shows an example of notification information indicating that the observation has not been performed properly; and FIG. 7 shows an example of notification information indicating that the observation has not been performed properly.

DETAILED DESCRIPTION OF THE INVENTION

The invention will now be described by reference to the preferred embodiments. This does not intend to limit the scope of the present invention, but to exemplify the invention.

Figure 1:
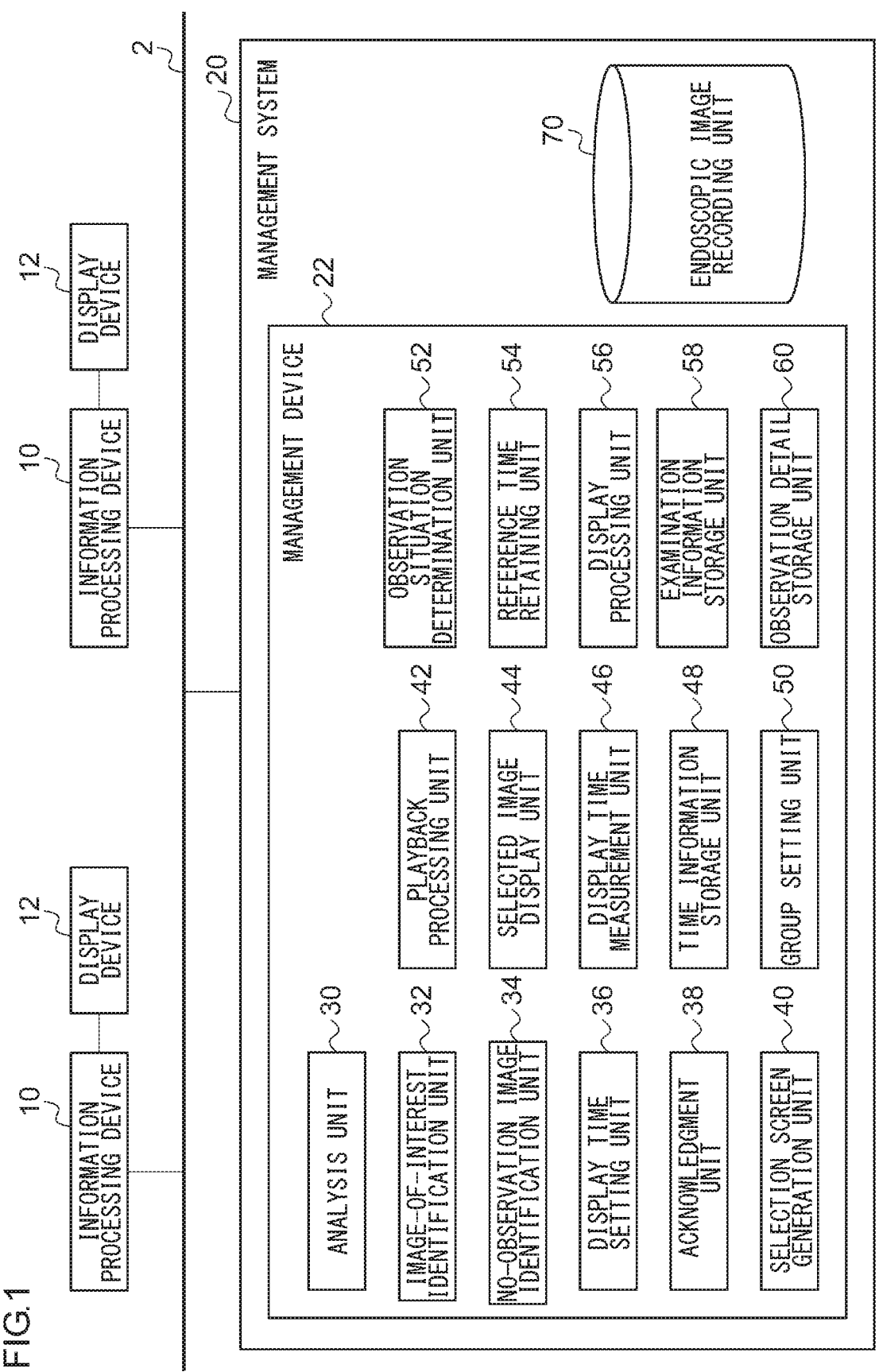
FIG. 1 shows a configuration of an endoscopic image observation support system according to an embodiment of the present invention.

FIG. 1 shows a configuration of an endoscopic image observation support system 1 according to an embodiment of the present invention. The endoscopic image observation support system 1 is a system for supporting the task of observing a capsule endoscopic image and is provided with a plurality of information processing devices 10 and a management system 20. The information processing device 10 is connected to the management system 20 via a network 2 exemplified by a local area network (LAN). For example, the information processing device 10 is a terminal device such as a personal computer assigned to a doctor or a technician and is connected to a display device 12 to enable an output to be displayed on the screen. The information processing device 10 may be a laptop computer integrated with a display device or a portable tablet.

The management system 20 is provided with a management device 22 for controlling playback and display of a capsule endoscopic image and an endoscopic image recording unit 70 for recording an endoscopic image captured by a capsule endoscope. Identification information (image ID) is assigned to each endoscopic image. Numerals included in the image ID represent the order of imaging in a capsule endoscopic examination by being incremented by 1 every time an image is captured. For example, an image ID "1" may be assigned to an endoscopic image captured first, and an image ID "2" may be assigned to an endoscopic image captured second so that the numeral included in the image ID may directly represent the order of capturing images.

The endoscopic image recording unit 70 may be comprised of a hard disk drive (HDD) or a flash memory. Still images totaling 10000~200000 are captured in one session of capsule endoscopic examination. Therefore, the endoscopic image recording unit 70 needs to be configured as a large capacity database. The information processing device 10 accesses the management system 20 to display the endoscopic images recorded in the endoscopic image recording unit 70 on the display device 12.

The management device 22 is provided with an analysis unit 30, an image-of-interest identification unit 32, a no-observation image identification unit 34, a display time setting unit 36, an acknowledgment unit 38, a selection screen generation unit 40, a playback processing unit 42, a selected image display unit 44, a display time measurement unit 46, a time information storage unit 48, a group setting unit 50, an observation situation determination unit 52, a reference time retaining unit 54, a display processing unit 56, an examination information storage unit 58, and an observation detail storage unit 60. The examination information storage unit 58 stores examination order information on a patient. The acknowledgment unit 38 acknowledges a user input entered by an image interpreter from the information processing device 10.

The features are implemented in hardware such as an arbitrary processor, a memory, or other LSI's and in software such as a program loaded into a memory. The figure depicts functional blocks implemented by the cooperation of these elements. Therefore, it will be understood by those skilled in the art that the functional blocks may be implemented in a variety of manners by hardware only, software only, or by a combination of hardware and software. Some of the functions shown in FIG. 1 as being those of the management device 22 may be implemented by the information processing device 10.

The functions of the management device 22 are implemented by running respective applications such as an analysis application, playback application, and observation situation determination application. The functions of the analysis unit 30, the image-of-interest identification unit 32, the no-observation image identification unit 34, and the display time setting unit 36 are implemented by the analysis application. The functions of the selection screen generation unit 40, the playback processing unit 42, the selected image display unit 44, and the observation detail storage unit 60 are implemented by the playback application. In the embodiment, the observation situation determination application for determining a situation of observation by an image interpreter is executed. The functions of the display time measurement unit 46, the time information storage unit 48, the group setting unit 50, the observation situation determination unit 52, the reference time retaining unit 54, and the display processing unit 56 are implemented by the observation situation determination application.

One of the purposes of a capsule endoscopic examination is to find a bleeding point in a digestive tract. Since images totaling 10000~200000 are captured in a capsule endoscopic examination, an enormous amount of time will be consumed if all images are observed for the same duration of time. To support efficient observation, the analysis application subjects endoscopic images to image analysis to extract a reddish endoscopic image considered to capture a bleeding state and identify such an image as an image of interest. Providing alert information related to an image of interest to an image interpreter during observation enables the image interpreter to observe the image of interest carefully.

The moving speed of the capsule endoscope in a digestive tract varies depending on the location. Where the moving speed is low, the variation between endoscopic images captured is small. In this background, the analysis application compares endoscopic images captured successively in time to find the variation. If the variation is small, the analysis application reduces the display time consumed as the images are switched and displayed sequentially. This ensures that images at a location of a small variation are switched at a high speed and played back accordingly to reduce the overall observation time. Further, the analysis application calculates the amount of food debris included in endoscopic images and identifies endoscopic images capturing a location where the food debris is in a large amount. The analysis application identifies such endoscopic images as no-observation images for which observation is not necessary.

The playback application performs sequential playback (also called sequential switching playback) whereby a plurality of endoscopic images are played back by being switched according to the order of imaging. The endoscopic images are displayed by being switched in the order that they were captured. Alternatively, the images may be switched in the order opposite to the order of imaging. By switching between a plurality of endoscopic images with small image-to-image variations at a high speed and playing back the images accordingly, the observation time for the image interpreter can be reduced. Endoscopic images capturing a large amount of food debris may be controlled not to be played back. By exercising such control, the observation time for the image interpreter is reduced and the load imposed on the image interpreter for observation is reduced. The playback application has a function of adjusting the playback speed in response to an instruction for playback from the information processing device 10 (e.g., an instruction for normal playback, an instruction for fast-forward playback, an instruction for fast-backward playback, an instruction for pause, etc.).

After the observation, the observation situation determination application determines whether the observation has been performed properly. The determination may be made for each endoscopic image or for a group of endoscopic images. In the embodiment, the observation situation determination application measures the display time of the endoscopic image and identifies the measured time as the observation time of the image interpreter. The observation situation determination application generates an evaluation score of the situation of observation by the image interpreter by determining whether the observation time is sufficient.

The information processing device 10 supports image observation by the image interpreter in cooperation with the management system 20. A user interface such as a keyboard and a mouse is connected to the information processing device 10. The information processing device 10 causes the display device 12 to display an observation screen. The image interpreter views the displayed screen and uses the user interface to input the observation detail. The observation detail represents a selection of an endoscopic image found to include a pathological change. The selected image is used in an image interpretation report.

The image interpreter observes 10000~200000 endoscopic images captured and selects an endoscopic image found to include a pathological change. In the embodiment, double image interpretation by a combination of a technician and a doctor is performed. The technician and the doctor perform image observation respectively and create an image interpretation report. Generally, image interpretation means observing images and making a diagnosis. However, the role of the technician in double image interpretation according to the embodiment is the assistance work of diagnostic imaging comprised of selecting an image found to include an abnormality and inputting finding information and is not the act of diagnosis. In this sense, the technician is an image interpretation assistant who does not make a diagnosis, but the technician as well as the doctor will be referred to as an image interpreter hereinafter.

In the embodiment, the technician performs image observation first, and then the doctor performs image observation. When the doctor performs image observation, the detail of observation performed by the technician earlier is reflected in the display screen. The doctor performs image observation by referring to the detail of observation by the technician, and, more particularly, to the image selected by the technician. By including a score of evaluation of the observation situation of image observation by the technician in the display screen, the doctor can know whether the observation by the technician has been performed properly.

When the endoscopic images captured by the capsule endoscope are recorded in the endoscopic image recording unit 70, the analysis unit 30 searches for a reddish endoscopic image considered to capture a bleeding state through image analysis. The image-of-interest identification unit 32 identifies the reddish image identified by the search as an image of interest. Further, the analysis unit 30 searches for an endoscopic image capturing a large amount of food debris. A pathological change cannot be observed in an endoscopic image capturing a large amount of food debris so that observation by the image interpreter is a waste of time. Therefore, the analysis unit 30 calculates a debris ratio for each endoscopic image. The no-observation image identification unit 34 identifies an endoscopic image where the debris ratio exceeds a predetermined value as a no-observation image.

The analysis unit 30 also extracts a plurality of endoscopic images captured successively and showing small image-to-image variations. The capsule endoscope captures images at a predetermined period. Therefore, if the moving speed is low, similar (substantially unvarying) images will be captured successively. Thus, the analysis unit 30 extracts a group of endoscopic images with small image-to-image variations and ensures that the switchover time between those endoscopic images sequentially played back is affected accordingly. The display time setting unit 36 sets the display time of the endoscopic image displayed by the playback processing unit 42 on the display device 12 in accordance with the order of imaging. For example, the display time setting unit 36 defines the display time of an ordinary endoscopic image to be 0.5 seconds. For a group of endoscopic images for which it is determined that image-to-image variations are small, the display time setting unit 36 defines the display time of each endoscopic image to be 0.1 seconds. The playback processing unit 42 switches between endoscopic images in accordance with the display time set by the display time setting unit 36 and displays the images accordingly. Thus, a group of images with small image-to-image variations are played back at a high speed to reduce the overall observation time.

In this example, the analysis unit 30 detects a group of endoscopic images captured when the moving speed of the capsule endoscope is determined to be low through image analysis. An acceleration sensor may be provided in the capsule endoscope and acceleration information may be recorded in each endoscopic image, thereby allowing the analysis unit 30 to calculate the moving speed. By recording acceleration information from the acceleration sensor in each endoscopic image, the analysis unit 30 can calculate the moving speed occurring while each endoscopic image is being captured and identify an endoscopic image captured when the moving speed is low.

As disclosed in JP2015-77234, the positions of a plurality of antennas fixed to the patient are fixed so that the position of the capsule endoscope is estimated by using the signal levels (received signal intensity) received by the respective antennas. During a capsule endoscopic examination, the signal levels of the plurality of antennas occurring while endoscopic images are being captured may be recorded in the respective endoscopic images captured. The analysis unit 30 may estimate the position of the capsule endoscope in the body by referring to the signal levels of the plurality of antennas recorded in the respective endoscopic images. Once the position of the capsule endoscope is estimated, the distance of movement that occurs between images can be calculated. Since the period of imaging of endoscopic images is constant, the analysis unit 30 can also calculate the moving speed of the capsule endoscope. Therefore, the analysis unit 30 can identify endoscopic images captured when the moving speed is low.

As described above, the analysis unit 30 can calculate the moving speed of the capsule endoscope occurring while images are being captured. In response to the result of calculation, the display time setting unit 36 defines the display time of endoscopic images captured when the moving speed is low to be 0.1 seconds and defines the display time of the other endoscopic images to be 0.5 seconds. The display time setting unit 36 may define the display time of endoscopic images captured when the moving speed is high to be longer than 0.5 seconds (e.g., 3 seconds). Thus, by using the display time setting unit 36 to set the display time of each endoscopic image, the management device 22 supports efficient observation.

An example of practicing double image interpretation by a technician B and a doctor C will be described below. The technician B enters the user ID and the password to log into the information processing device 10. When the technician B logs in, the management device 22 supplies examination information stored in the examination information storage unit 58 to the information processing device 10, and the display device 12 displays a list of capsule endoscopic examinations. The list of examinations lists examination information such as the patient ID, patient name, examination ID, date and time of examination, and the technician B selects an examination in which the technician B is expected to assist in diagnostic imaging. When an examination for a patient A and with an examination ID "0001" is selected from the list of examinations, the selection screen generation unit 40 generates a selection screen for selecting an endoscopic image and causes the display device 12 to display the selection screen. The function of the selection screen generation unit 40 may be provided in the information processing device 10.

Figure 2:
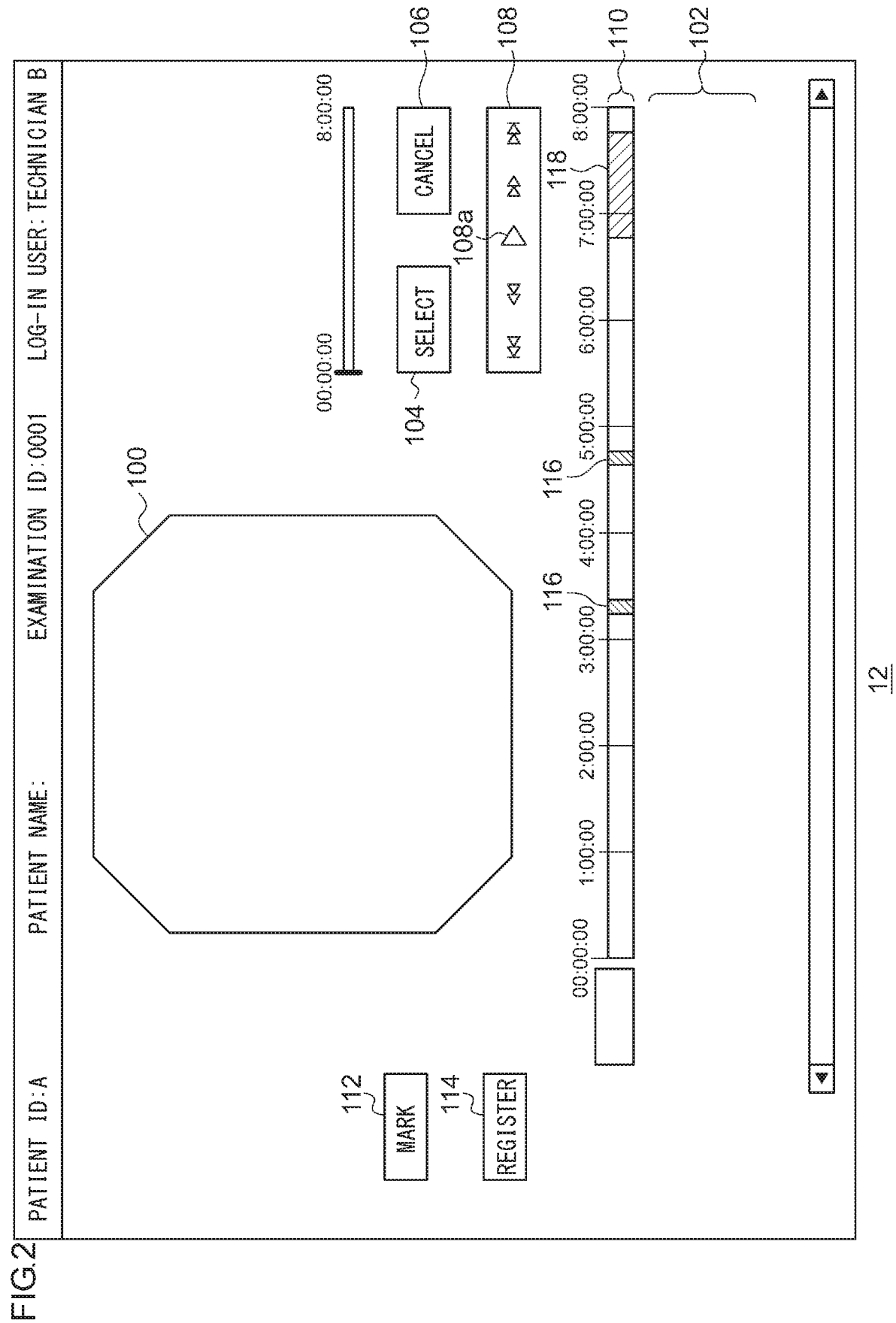
FIG. 2 shows an example of a selection screen for selection of an endoscopic image.

FIG. 2 shows an example of a selection screen for selection of an endoscopic image. The selection screen generation unit 40 generates a selection screen that includes a playback area 100 for displaying endoscopic images successively. Buttons for controlling the playback operation are displayed in a playback user operation area 108 to enable adjustment of the playback speed. When a playback button 108*a* is used, switching display of endoscopic images in the playback area 100 is started. In the playback user operation area 108, a pause button is displayed in pace of the playback button 108*a*. A user operation input in the playback user operation area 108 is transmitted from the information processing device 10 to the management device 22 and acknowledged by the acknowledgment unit 38.

When the technician B uses the pause button while endoscopic images are displayed in the playback area 100 successively, the switching between endoscopic images is suspended. When the technician B uses the mouse wheel in this state, the image before or after the paused endoscopic image is displayed in the playback area 100. When the technician B uses a selection button 104 while the endoscopic image is being paused in the playback area 100, the image is captured and displayed in a selected image display area 102. The selected image displayed in the selected image display area 102 may be selected as an image attached to an image interpretation report later. The technician B may select the selected image in the selected image display area 102 and use a cancel button 106 to cancel the selection. For example, the cancel button 106 may be used to maintain only a properly captured image if a plurality of images including the same finding are selected.

A timeline 110 is a user interface to indicate the temporal position of the endoscopic image displayed in the playback area 100 and is also a user interface to display an endoscopic image in the playback area 100 in a pause state. When the technician B places the mouse pointer at a desired section on the timeline 110, the endoscopic image captured at that point of time is displayed in the playback area 100. The technician B can add a mark in the timeline 110 to indicate a position where a body part starts. The technician B viewing endoscopic images played back sequentially in the playback area 100 and finding that a new body part is played back uses a marking button 112 to mark the position of start of the body part on the timeline. By allowing the technician B performing image observation first in double image interpretation to mark the position of start of each body part, the doctor C performing image observation later can know the position of start of the body part by referring to the mark.

An image-of-interest range 116 on the timeline 110 indicates a temporal range of an image-of-interest identified by the image-of-interest identification unit 32. The image-of-interest range 116 is displayed on the timeline 110 as alert information colored in red and alerts the image interpreter of an image of interest. In this example, the temporal ranges of two images of interest are displayed on the timeline 110. The image interpreter observes the images recorded in the image-of-interest ranges 116 more carefully than other images.

Meanwhile, a no-observation image range 118 indicates the temporal range of an image identified by the no-observation image identification unit 34 as requiring no observation. As described above, a no-observation image is an image capturing a location where the food debris is in a large amount and so cannot be observed in any substantive manner. Accordingly, the playback processing unit 42 may exercise playback control whereby no-observation images, for which observation is of little significance, are excluded. The image interpreter can of course observe the image in the no-observation image range 118 if so wishes.

Figure 3:
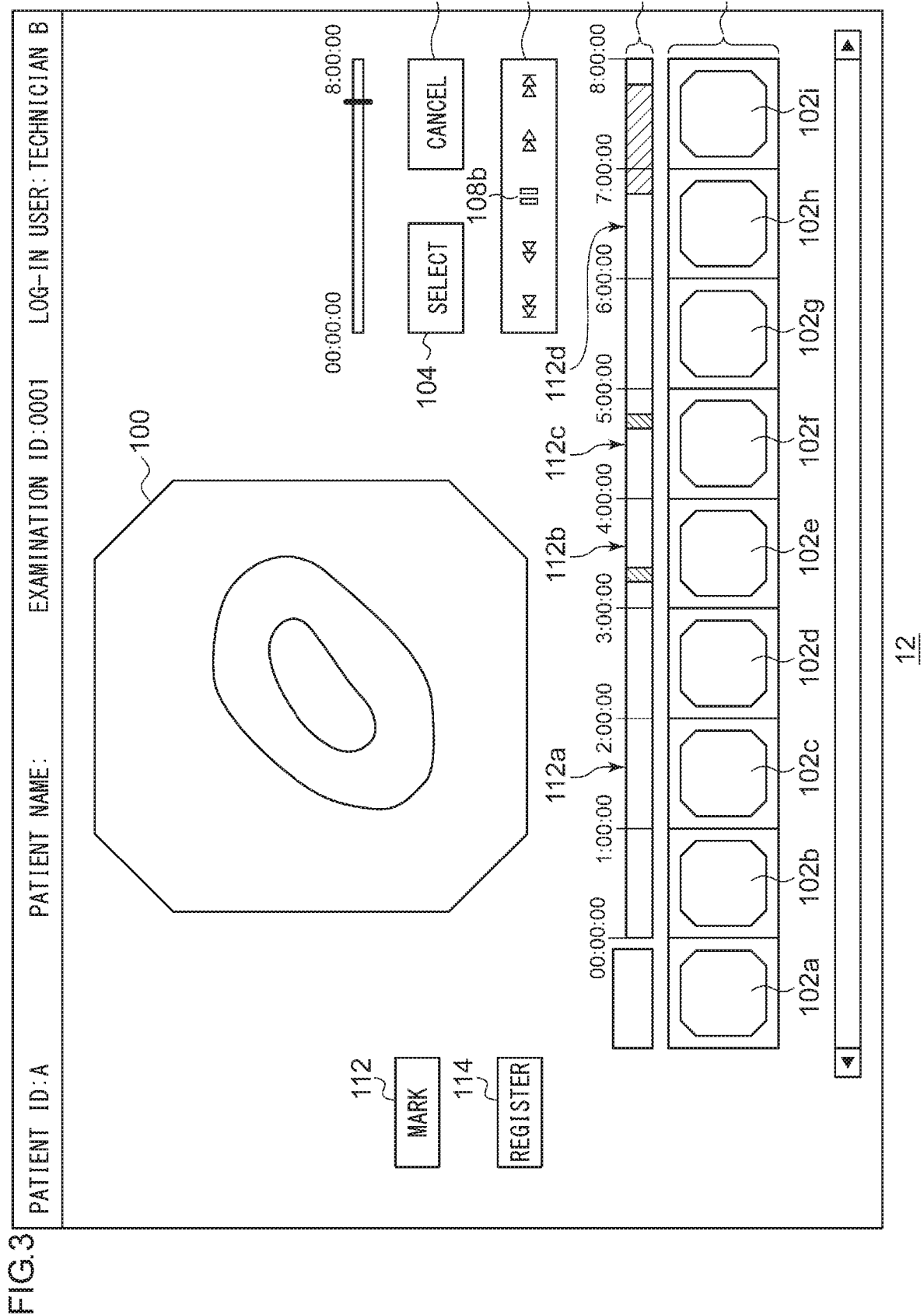
FIG. 3 shows an example of a selection screen occurring while endoscopic images are sequentially displayed.

FIG. 3 shows an example of a selection screen occurring while endoscopic images are sequentially displayed. The playback processing unit 42 displays endoscopic images recorded in the endoscopic image recording unit 70 in the playback area 100. As mentioned above, the display time setting unit 36 sets the display time of endoscopic images displayed by the playback processing unit 42 on the display device 12 in accordance with the order of imaging. The display time setting unit 36 sets the display time of endoscopic images in accordance with the moving speed of the capsule endoscope occurring while the image is being captured. The display time setting unit 36 may define the display time of the endoscopic image captured when the moving speed is high to be longer and define the display time of the endoscopic image captured when the moving speed is low to be shorter. The display time set by the display time setting unit 36 is used by the playback processing unit 42, and the playback processing unit 42 successively displays endoscopic images in the playback area 100 in accordance with the display time as set. This allows the image interpreter to observe endoscopic images as if they were moving images.

The technician B uses the marking button 112 while observing images to mark the positions of start of body parts. A mark 112*a* indicates the start of the stomach, a mark 112*b* indicates the start of the duodenum, a mark 112*c* indicates the start of the jejunum, and a mark 112*d* indicates the start of the colon. The technician B viewing endoscopic images played back successively in the playback area 100 and finding that a new body part is played back uses the marking button 112 to mark the position of start of the body part on the timeline.

When an image found to include a pathological change is displayed in the playback area 100, the technician B uses a pause button 108*b* to stop switching between displayed images. When the pause button 108*b* is used, the playback button 108*a* is displayed in the playback user operation area 108 in place of the pause button 108*b*. The technician B uses the mouse wheel to cause images before and after the paused image to be displayed in the playback area 100 and searches for an image that captures a pathological change clearly. The acknowledgment unit 38 in the management device 22 acknowledges a user operation input, and, more specifically, a button operation or a mouse wheel operation. The playback processing unit 42 causes the endoscopic image to be displayed on the display device 12 in accordance with a user operation input acknowledged by the acknowledgment unit 38.

When the image found to capture a pathological change clearly is displayed in the playback area 100, the technician B uses the selection button 104. When the acknowledgment unit 38 in the management device 22 acknowledges the selection operation, the selected image display unit 44 captures the selected image displayed in the playback area 100 and displays it in the selected image display area 102. The selected image displayed in the selected image display area 102 may be selected as an image attached to an image interpretation report later.

Of the various pathological changes found to be captured, it is imperative that the technician B select an image capturing a bleeding point. The technician B observes the image-of-interest range 116 displayed on the timeline 110 and the neighborhood thereof carefully and identifies an image capturing a bleeding point. By causing the image-of-interest identification unit 32 to identify an endoscopic image capturing a bleeding state as an image of interest in advance, the risk of overlooking by the image interpreter can be reduced. FIG. 3 shows that selected images 102*a*-102*i* are selected in the selected image display area 102.

The technician B having finished observing the images uses a registration button 114. When registration button 114 is used, the selected image selected in the selected image display area 102 and time information indicating the positions of start of the body parts marked by using the marking button 112 are stored in the observation detail storage unit 60 in the management system 20. This completes the image observation by the technician B.

In the embodiment, the observation situation determination application determines whether the situation of observation by the technician B is proper after the image observation by the technician B is completed. As an indicator for determination as to properness, the observation situation determination application measures the display time of the endoscopic images and determines whether the display time is proper, i.e., whether sufficient time was consumed for observation.

While the technician B is observing images, the display time measurement unit 46 measures the display time of each endoscopic image. The playback processing unit 42 switches between endoscopic images and displays the endoscopic images in the playback area 100. The display time measurement unit 46 measures the time that each endoscopic image is displayed in the playback area 100. When the playback button 108*a* is used, the playback processing unit 42 displays the endoscopic image in accordance with the display time set by the display time setting unit 36. When a fast-forward playback button is used, the playback processing unit 42 displays endoscopic images successively by reducing the display time set by the display time setting unit 36. Thus, the display time of the endoscopic image is adjusted in accordance with a user operation entered by the image interpreter. The display time measurement unit 46 measures the real display time of each endoscopic image. When the pause button 108*b* is used, the playback processing unit 42 pauses the endoscopic image. Therefore, the paused endoscopic image is measured as being displayed for a long period of time.

The time information storage unit 48 stores information related to the display time measured by the display time measurement unit 46. During image observation, the technician B pauses playback by the playback processing unit 42 and causes the paused image and images before and after to be displayed in the playback area 100 by using the mouse wheel. The display time measurement unit 46 cumulatively measures the display time of each endoscopic image. Therefore, an endoscopic image displayed a plurality of times or an endoscopic image that continues to be displayed in the playback area 100 is measured as being displayed for a long period of time.

In the embodiment, the display time is stored in the time information storage unit 48 as an indicator to evaluate whether the observation has been performed sufficiently. The playback processing unit 42 displays the endoscopic image in the playback area 100 in accordance with a user operation input of the image interpreter acknowledged by the acknowledgment unit 38, and the time information storage unit 48 stores information related to the cumulative display time of each endoscopic image. This ensures that, when the technician B finishes observing the images, the time information storage unit 48 stores the information related to the cumulative display time of all endoscopic images.

A description will now be given of image observation by the doctor C. The doctor C enters the user ID and the password to log into the information processing device 10. When the doctor C logs in, the management device 22 supplies examination information stored in the examination information storage unit 58 to the information processing device 10, and the display device 12 displays a list of capsule endoscopic examinations. When an examination for a patient A and with an examination ID "0001" is selected from the list of examinations, the selection screen generation unit 40 generates a selection screen for selecting an endoscopic image and causes the display device 12 to display the selection screen.

Figure 4:
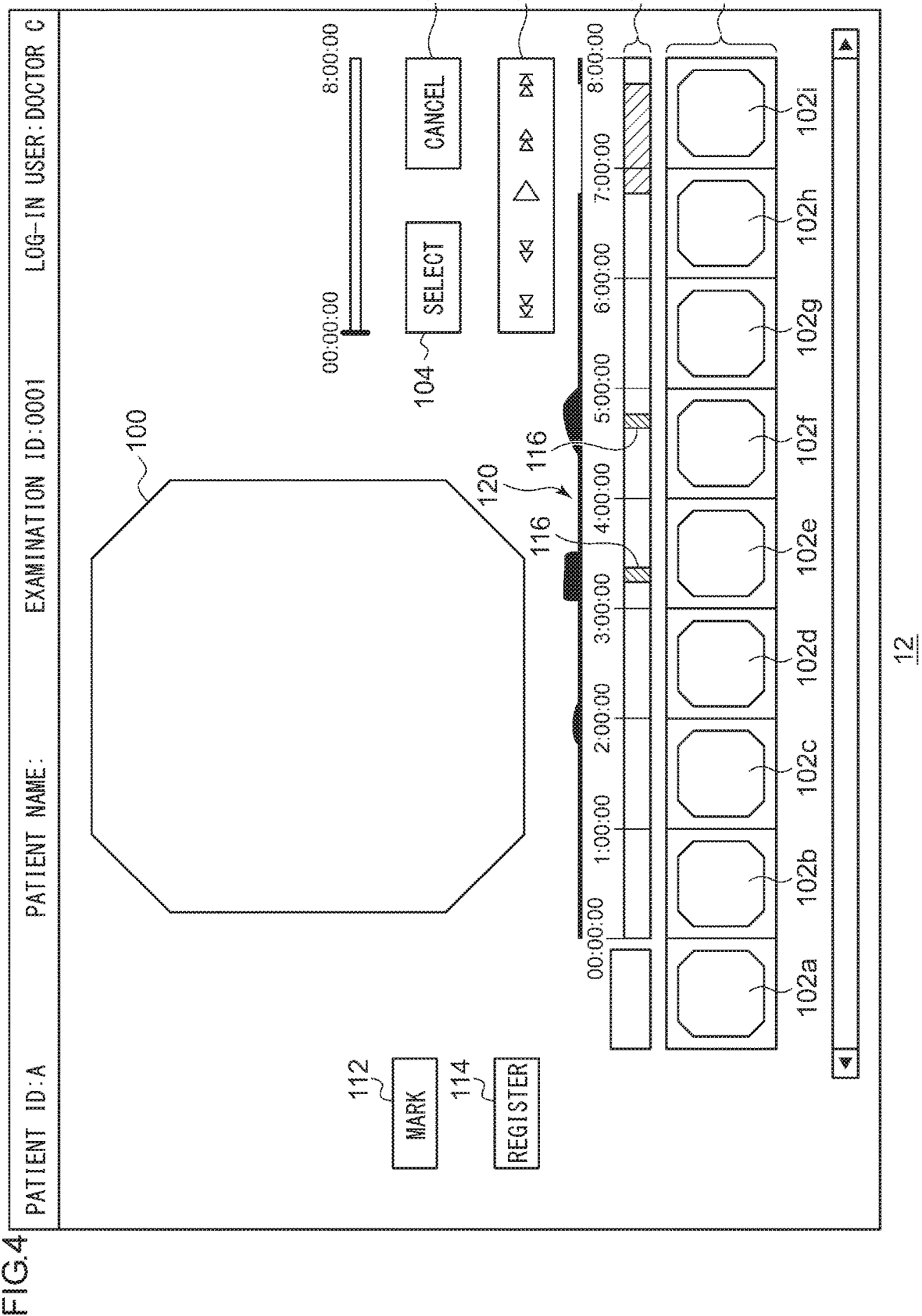
FIG. 4 shows an example of a selection screen for selection of an endoscopic image.

FIG. 4 shows an example of a selection screen for selection of an endoscopic image. The selection screen generation unit 40 generates a selection screen that includes a playback area 100 for displaying endoscopic images successively. The selection screen generation unit 40 acquires the selected images stored in the observation detail storage unit 60 through the image observation by the technician B and the time information indicating the positions of start of the respective body parts. The selection screen generation unit 40 displays the marks 112*a*-112*d* and the selected images 102*a*-102*i*. The doctor C can know the positions of start of the respective body parts by referring to the marks 112*a*-112*d* placed by the technician B.

The display processing unit 56 reads the cumulative display time of each endoscopic image stored in the time information storage unit 48 and presents it in the form of a graph in the observation situation display area 120. The observation situation display area 120 is provided along the timeline 110. The horizontal axis represents the time that the endoscopic image is captured, and the vertical axis represents the cumulative display time. When the doctor C opens the selection screen, the display processing unit 56 presents the cumulative display time of each endoscopic image observed by the technician B in the observation situation display area 120 in the form of a graph. Thus, the doctor C can know the situation of observation by the technician B. In this example, it is indicated that the technician B took time to observe images near the image-of-interest range 116 and the image-of-interest range 116. The doctor C knows that the technician B observed the image-of-interest ranges 116 and the neighborhood thereof carefully.

In the example shown in FIG. 4, the observation situation display area 120 displays the cumulative display time, but the display processing unit 56 may display information indicating whether the image observation by the technician B was proper. The observation situation determination unit 52 determines whether the observation has been performed properly based on the reference observation time stored in the reference time retaining unit 54 and the time information stored in the time information storage unit 48.

FIG. 5A shows examples of reference observation time retained in the reference time retaining unit 54. The reference observation time represents the minimum period of time required for observation. The image interpreter is required to observe the image for at least the duration of the reference observation time. In this example, the reference time retaining unit 54 retains the reference observation time determined by the moving speed of the capsule endoscope occurring while the image is being captured. In this case, the reference observation time for the image captured during a high-speed movement is set to be 3 seconds, the reference observation time for the image captured during a normal-speed movement is set to be 0.5 seconds, the reference observation time for the image captured during a low-speed movement is set to be 0.1 seconds. The analysis unit 30 analyzes the endoscopic images in advance and calculates the moving speed of the capsule endoscope occurring while each endoscopic image is being captured. For example, the analysis unit 30 may evaluate a speed less than a speed V1 per hour to be a low speed, a speed equal to or higher than the speed V1 per hour and less than a speed V2 per hour to be a normal speed, and a speed equal to or higher than the speed V2 per hour to be a high speed and may set the evaluation as attribution information for each endoscopic image (V1<V2).

Images captured by the capsule endoscopic image during a high-speed movement are distanced from each other. Therefore, the likelihood of overlooking a pathological change is high, and careful observation is required. For this reason, the reference time retaining unit 54 sets the reference observation time of the image captured during a high-speed movement to be long (3 seconds). A standard-speed playback duration of 0.5 seconds is set for the image captured by the capsule endoscope moving at a normal speed, and a high-speed playback duration of 0.1 seconds is set for the image captured by the capsule endoscope moving at a low speed. The display time setting unit 36 may set the display time of the image captured during a high-speed movement to 3 seconds.

The observation situation determination unit 52 compares the reference observation time retained in the reference time retaining unit 54 and the cumulative display time stored in the time information storage unit 48 and determines whether the cumulative display time of each endoscopic image is equal to or longer than the reference observation time. If the cumulative display time of all endoscopic images is equal to or longer than the reference observation time associated with the moving speed of the capsule, the observation situation determination unit 52 determines that all endoscopic images have been observed properly. Meanwhile, if there are any endoscopic images for which the cumulative display time is less than the reference observation time, the observation situation determination unit 52 determines that some endoscopic images have not been observed properly.

When the observation situation determination unit 52 determines that the observation has not been performed properly, the display processing unit 56 causes the display device 12 to display information indicating that the observation has not been performed properly. FIG. 6 shows an example of notification information 122 indicating that the observation has not been performed properly. The notification information 122 is displayed relative to the timeline 110 as image position information indicating that the observation has not been performed properly. When the selection screen is displayed, the doctor C refers to the observation situation display area 120 and the notification information 122 and recognizes that some endoscopic images have not been observed properly by the technician B. In this way, the doctor C can know that at least the image indicated by the notification information 122 needs to be observed carefully.

As shown in FIG. 5A, the reference time retaining unit 54 may retain the reference observation time for endoscopic images captured when the moving speed of the capsule endoscope is relatively high, the reference observation time for endoscopic images captured when the moving speed of the capsule endoscope is relatively low, and the reference observation time for the other endoscopic images. The observation situation determination unit 52 may determine whether proper observation associated with the moving speed of the capsule endoscope has been performed.

FIGS. 5B and 5C show examples where the reference time retaining unit 54 retains the reference observation time for the image of interest and nearby images near the image of interest in the order of imaging. In the embodiment, the image of interest is an image considered to capture a bleeding state. There is a high probability that an image capturing a bleeding point is included in the image of interest and/or the nearby images. In this background, the endoscopic image observation support system 1 predefines the reference observation time for the image of interest and the nearby images. If the cumulative display time of the image of interest and the nearby images has not reached the reference observation time, the observation situation determination unit 52 determines that sufficient observation has not been performed. If the reference observation time has been reached, the observation situation determination unit 52 determines that sufficient observation has been performed.

FIG. 5B shows another example of the reference observation time retained in the reference time retaining unit 54. In this example, the reference time retaining unit 54 retains the reference observation time for the image of interest and images near the image of interest. In this case, the reference observation time for the image of interest is set to be 7 seconds, the reference observation time for the image capturing an area 3 cm or less from the image of interest is set to be 5 seconds, and the reference observation time for the image capturing an area more than 3 cm and equal to or less than 7 cm is set to be 2 seconds. The analysis unit 30 analyzes the endoscopic images in advance and estimates the position of the capsule endoscope occurring while each endoscopic image is being captured. The image-of-interest identification unit 32 identifies a reddish image of interest. This allows the observation situation determination unit 52 to identify the image of interest and the nearby images located within a predetermined distance from the image of interest.

The image of interest is considered to capture a bleeding state and so needs to be observed carefully. It is likely that images near the image of interest also capture a bleeding point. Therefore, the closer the nearby image to the image of interest, the more carefully it is necessary to observe the nearby image. Accordingly, in the example shown in FIG. 5B, the nearby images are grouped into two categories. The reference observation time for the nearby images closer to the image of interest is set to be 5 seconds, and the reference observation time for the nearby images further away is set to be 2 seconds.

The observation situation determination unit 52 compares the reference observation time retained in the reference time retaining unit 54 and the cumulative display time stored in the time information storage unit 48 and determines whether the cumulative display time of each endoscopic image is equal to or longer than the reference observation time. If the cumulative display time of the relevant endoscopic images is equal to or longer than the reference observation time shown in FIG. 5B, the observation situation determination unit 52 determines that all relevant endoscopic images have been observed properly. Meanwhile, if there are any endoscopic images for which the cumulative display time is less than the reference observation time, the observation situation determination unit 52 determines that some endoscopic images have not been observed properly.

The group setting unit 50 may group the endoscopic images that meet the conditions shown in FIG. 5B, and the observation situation determination unit 52 may determine whether the observation was performed for a duration defined by the reference observation time or longer for each group. The group setting unit 50 defines one or more images of interest as belonging to the first group, one or more nearby images captured at a distance of 3 cm or less upstream from the first group as belonging to the second group, one or more nearby images captured in a range of 3 cm~7 cm upstream of the first group as belonging to the third group, one or more nearby images captured at a distance of 3 cm or less downstream from the first group as belonging to the fourth group, and one or more images captured in a range of 3 cm~7 cm downstream from the first group as belonging to the fifth group. The observation situation determination unit 52 may determine that the observation has been performed properly if the cumulative display time of any one of the endoscopic images belonging to each group is found to be equal to or longer than the reference observation time for the group. If three endoscopic images are included in one group, it is determined that the observation for that group has been performed properly if the cumulative display time of a single endoscopic image is equal to or longer than the reference observation time. Thus, the act of observing the image of interest and the nearby images may be evaluated group by group.

If at least one of the image of interest and the nearby images is captured and included in the selected image display area 102, the observation situation determination unit 52 may determine that the observation has been performed properly regardless of the cumulative display time. This is because the purpose of observation is to select an image found to include an abnormality, and a determination that the observation has been performed properly does not pose any problem if the image is selected.

FIG. 5C shows another example of the reference observation time retained in the reference time retaining unit 54. In this example, the reference time retaining unit 54 retains the reference observation time for the image of interest and images near the image of interest. In this case, the reference observation time for the image of interest is set to be 7 seconds, the reference observation time for the nearby image captured at an interval of 5 seconds or less from when the image of interest was captured is set to be 5 seconds, and the reference observation time for the nearby image captured at an interval longer than 5 seconds and equal to less than 10 seconds from when the image of interest was captured is set to be 2 seconds. In the embodiment, the capsule endoscope periodically captures images inside the body. Therefore, the observation situation determination unit 52 identifies the image of interest and the nearby images captured within a predetermined interval from when the image of interest was captured by referring to the image IDs.

The observation situation determination unit 52 compares the reference observation time retained in the reference time retaining unit 54 and the cumulative display time stored in the time information storage unit 48 and determines whether the cumulative display time of each endoscopic image is equal to or longer than the reference observation time. If the cumulative display time of the relevant endoscopic images is equal to or longer than the reference observation time shown in FIG. 5C, the observation situation determination unit 52 determines that all relevant endoscopic images have been observed properly. Meanwhile, if there are any endoscopic images for which the cumulative display time is less than the reference observation time, the observation situation determination unit 52 determines that some endoscopic images have not been observed properly.

The group setting unit 50 may group the endoscopic images that meet the conditions shown in FIG. 5C, and the observation situation determination unit 52 may determine whether the observation was performed for a duration defined by the reference observation time or longer for each group. The group setting unit 50 defines one or more images of interest as belonging to the first group, one or more nearby images captured upstream of the first group and at an interval of 5 seconds or less from when the image of interest was captured as belonging to the second group, one or more nearby images captured upstream of the first group and at an interval of more than 5 seconds and equal to or less than 10 seconds from when the image of interest was captured as belonging to the third group, one or more nearby images captured downstream of the first group and at an interval of 5 seconds or less from when the image of interest was captured as belonging to the fourth group, and one or more nearby images captured downstream of the first group and at an interval of more than 5 seconds and equal to or less than 10 seconds from when the image of interest was captured as belonging to the fifth group. The observation situation determination unit 52 may determine that the observation has been performed properly if the cumulative display time of any one of the endoscopic images belonging to each group is found to be equal to or longer than the reference observation time for the group. If three endoscopic images are included in one group, it is determined that the observation for the group has been performed properly if the cumulative display time of a single endoscopic image is equal to or longer than the reference observation time. Thus, the act of observing the image of interest and the nearby images may be evaluated group by group.

If at least one of the image of interest and the nearby images is captured and included in the selected image display area 102, the observation situation determination unit 52 may determine that the observation has been performed properly regardless of the cumulative display time. This is because the purpose of observation is to select an image found to include an abnormality, and a determination that the observation has been performed properly does not pose any problem if the image is selected.

Thus, if the reference time retaining unit 54 retains the reference observation time shown in FIG. 5B or FIG. 5C, the observation situation determination unit 52 determines whether the observation has been performed properly based on time information on the nearby images captured within a predetermined distance from where the image of interest was captured or the time information on the nearby images captured within a predetermined period of time from when the image of interest was captured. In this way, the properness of the situation of observing the image of interest is evaluated.

When the observation situation determination unit 52 determines that the observation has not been performed properly, the display processing unit 56 causes the display device 12 to display information indicating that the observation has not been performed properly. FIG. 7 shows an example of notification information 124 indicating that the observation has not been performed properly. The notification information 124 is displayed relative to the timeline 110 as image position information indicating that the observation has not been performed properly. When the selection screen is displayed, the doctor C refers to the observation situation display area 120 and the notification information 124 and recognizes that some endoscopic images have not been observed properly by the technician B. In this way, the doctor C can know that at least the image indicated by the notification information 124 needs to be observed carefully.

The reference time retaining unit 54 may retain the reference observation time for the endoscopic image of a body part of interest. The body part of interest is designated by the doctor as being a body part where a pathological change is likely to be found based on the major complaint by the patient. For example, when the doctor suspects Crohn disease from the major complaint, it is desirable to observe the ileum terminal carefully because it is highly likely that a pathological change is found in the ileum terminal. For this reason, the image-of-interest identification unit 32 identifies the endoscopic image captured at the ileum terminal, i.e., on the near side of the colon, as an image of interest based on the designation by the doctor. In this example, it is assumed that the reference observation time for the endoscopic image of the body part of interest is set to be the reference observation time for the image of interest shown in FIG. 5B or FIG. 5C, but the reference time retaining unit 54 may retain the reference observation time for the body part of interest separately.

The position of start of the colon is identified by the mark 112*d*. Therefore, the observation situation determination unit 52 determines whether the cumulative display time of the endoscopic images of the ileum terminal and the neighborhood captured before the mark 112*d* is equal to or longer than the reference observation time defined in FIG. 5B or FIG. 5C. If the cumulative display time is equal to or longer than the reference observation time, the observation situation determination unit 52 determines that the observation of the endoscopic image of the body part of interest by the technician B has been performed properly.

As described above, the doctor C can refer to the situation of observation by the technician B in the selection screen and perform image observation with the knowledge of the situation of observation by the technician B. Therefore, if it is indicated that the observation by the technician B is insufficient, the doctor C observes the insufficiently observed endoscopic image more carefully than the other images. The playback process by the management device 22 is as described in connection with the technician B. The doctor C observes the image displayed in the playback area 100 and, when the image found to include a pathological change is displayed in the playback area 100, the doctor C uses the pause button 108*b* to stop switching between displayed images and uses the selection button 104 to select the displayed image. Also, the doctor C can not only refer to the situation of observation by the technician B but also refer to the selected images 102*a*-102*i* selected by the technician B. Therefore, the doctor C can surmise the intent with which the technician B selected the image.

The doctor C having finished observing the images uses the registration button 114. When registration button 114 is used, the selected image selected in the selected image display area 102 is stored in the observation detail storage unit 60 in the management system 20. This completes the image observation by the doctor C.

The display time measurement unit 46 measures the display time of each endoscopic image while the doctor C is observing images, too. The playback processing unit 42 switches between endoscopic images and displays the endoscopic images in the playback area 100. The display time measurement unit 46 measures the time that each endoscopic image is displayed in the playback area 100.

The time information storage unit 48 stores information related to the display time measured by the display time measurement unit 46. It is preferable that the time information storage unit 48 store the information on the display time consumed by the doctor C and the information on the display time consumed by the technician B separately. The reference time retaining unit 54 retains the reference observation time for each endoscopic image. For evaluation of the observation situation in double image interpretation, the reference time retaining unit 54 may retain the reference observation time for each endoscopic image observed by two image interpreters. This reference observation time defines the minimum display time for the two image interpreters. For example, the total reference observation time of an image of interest may be defined to 20 seconds. The observation situation determination unit 52 totals the display time consumed by the technician B and the display time consumed by the doctor C stored in the time information storage unit 48 for each endoscopic image and may compare the totaled time with the reference observation time retained in the reference time retaining unit 54. For example, if the observation situation determination unit 52 determines that the observation time consumed by the two image interpreters has not reached the reference observation time when the doctor C uses the registration button 114, the display processing unit 56 may display information alerting that the observation time is insufficient on the display device 12. The observation situation determination unit 52 may total the display time consumed by the image interpreters for each group instead of for each endoscopic image and compare the totaled time with the reference observation time.

Described above is an explanation based on an exemplary embodiment. The embodiment is intended to be illustrative only and it will be understood by those skilled in the art that various modifications to constituting elements and processes could be developed and that such modifications are also within the scope of the present invention.

In the embodiment, the evaluation of the situation of observation by the technician B is described as being communicated to the doctor C. In one variation, when the technician B uses the registration button 114, the display processing unit 56 may notify the technician B accordingly.

In the embodiment, the no-observation image identified by the no-observation image identification unit 34 is described as not being displayed. Alternatively, the playback processing unit 42 may play back the no-observation image. In this case, it is not expected that sufficient observation can be made in the no-observation image. It is therefore preferable that the observation situation determination unit 52 does not examine the observation situation for the no-observation image.

What is claimed is:

1. An observation system comprising:
a processor comprising hardware, the processor being configured to:
record a plurality of endoscopic images captured by an endoscope;
acknowledge a user operation input;
cause a display device to display the recorded plurality of endoscopic images in accordance with the acknowledged user operation input;
measure a display time of each endoscopic image of the displayed plurality of endoscopic images;
store the measured display time of each endoscopic image of the displayed plurality of endoscopic images;
from the plurality of endoscope images, identify a first endoscopic image that captures a pathological change or body part of interest;
determine a first reference observation time for the first endoscopic image based on a predetermined criteria; and
determine whether the first endoscopic image has been observed properly based on a comparison between the determined first reference observation time and a first measured display time of the first endoscopic image from the stored measured display times, and generate an indicator to indicate a state regarding whether the first endoscopic image has been properly observed.

2. The observation system according to claim 1, wherein the processor is configured to:
identify a second endoscopic image, different from the first endoscopic image, from the plurality of endoscopic images that captures the pathological change or the body part of interest;
determine a second reference observation time for the second endoscopic image based on the predetermined criteria, the second reference observation time being shorter than the first reference observation time, and
determine whether the second endoscopic image has been observed properly based on the determined second reference observation time and a second measured display time of the second endoscopic image from the stored measured display times, and generate an indicator to indicate a state regarding whether the second endoscopic image has been properly observed.

3. The observation system according to claim 2, wherein the second endoscopic image is near the first endoscopic image in an order of imaging.

4. The observation system according to claim 1, wherein the processor is configured to determine the first reference observation time for the first endoscopic image based on the identified pathological change or identified body part of interest as the predetermined criteria.

5. The observation system according to claim 1, wherein the processor is further configured to set a display order of the recorded plurality of endoscopic images in accordance with an order of imaging.

6. The observation system according to claim 1, wherein the processor is further configured to cause the display device to display information indicating that the first endoscopic image has not been properly observed when it is determined that the first endoscopic image has not been properly observed.

7. The observation system according to claim 1, wherein the processor is further configured to:
identify a second endoscopic image, different from the first endoscopic image, for which observation is not necessary from among the recorded plurality of endoscopic images based on an other predetermined criteria different from the predetermined criteria, and
causes the display device to not display the identified second endoscopic image.

8. The observation system according to claim 1, wherein the endoscope is a capsule endoscope.

9. The observation system according to claim 1, wherein:
the predetermined criteria comprises a position of the endoscope corresponding to the plurality of endoscopic images, and
the processor is configured to:
receive an indication of the position of the endoscope corresponding to the plurality of endoscopic images; and
determine the first reference observation time based on the distance between images in a group of the plurality of endoscopic images that includes the first endoscopic image.

10. The observation system according to claim 1, wherein:
the predetermined criteria comprises a speed of the endoscope corresponding to the first endoscopic image, and
the processor is configured to:
receive an indication of the speed of the endoscope corresponding to the first endoscopic image; and
determine the first reference observation time based on the speed of the endoscope.

* * * * *